(12) United States Patent
Hassan et al.

(10) Patent No.: US 7,807,189 B2
(45) Date of Patent: Oct. 5, 2010

(54) SKIN CARE FORMULATION

(75) Inventors: Mahmoud Hassan, Somerset, NJ (US); Stacey Kaplan, East Brunswick, NJ (US); Nadia Soliman, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 1511 days.

(21) Appl. No.: 10/976,100

(22) Filed: Oct. 27, 2004

(65) Prior Publication Data

US 2006/0088557 A1    Apr. 27, 2006

(51) Int. Cl.
*A61K 8/02* (2006.01)
*A61K 9/00* (2006.01)
(52) U.S. Cl. ...................... 424/401; 424/400
(58) Field of Classification Search ................. 424/401, 424/400
See application file for complete search history.

(56) References Cited

U.S. PATENT DOCUMENTS

| | | | |
|---|---|---|---|
| 5,591,449 A * | 1/1997 | Bollens et al. | 424/450 |
| 6,042,815 A | 3/2000 | Kellner et al. | |
| 6,217,852 B1 * | 4/2001 | Gildenberg et al. | 424/59 |
| 6,699,488 B2 | 3/2004 | Deckner et al. | |

FOREIGN PATENT DOCUMENTS

| | | |
|---|---|---|
| EP | 0 765 656 | 4/1997 |
| EP | 1 247 565 | 10/2002 |
| WO | WO 01/62224 | 8/2001 |

OTHER PUBLICATIONS

Sharif et al. Archives of Disease in Childhood (2001); vol. 85, pp. 121-124.*
Sigma Catolgue Product Description Sheets (Brij 52, Triton X-100 and Sorbitan trioleate), 2007, pp. 1-2.*

* cited by examiner

*Primary Examiner*—Sreeni Padmanabhan
*Assistant Examiner*—Samira Jean-Louis
(74) *Attorney, Agent, or Firm*—Michael F. Morgan

(57) ABSTRACT

Skin moisturizing formulations which can be administered in the bath or shower, depositing a thin layer of moisturizing agents on application, which is not rinsed off but remains to protect the skin from drying, resulting in smoother, softer skin feel; the formulations comprising polyvalent metal cations and fatty acids, which react on application in the shower or bath to form a thin deposit of insoluble salts, thereby enhancing the retention of moisturizing oils and conditioning agents.

24 Claims, No Drawings

SKIN CARE FORMULATION

FIELD OF THE INVENTION

This invention relates to novel skin care formulations containing low concentrations of long chain acids, e.g., fatty acids, and polyvalent metal ions, suitable for use in the bath or shower and capable of delivering moisturizing and other beneficial ingredients to the skin and providing improved skin feel even after rinsing.

BACKGROUND OF THE INVENTION

Skin care compositions, for example skin moisturizing compositions, are typically aqueous formulations comprising an emulsified oil which is stabilized with surfactant. Ideally, moisturizing compositions are best applied to the skin when the skin is wet and saturated with water, but a disadvantage of conventional formulations in this respect is that they are immediately and entirely rinsed off when applied in the shower or bath. Oil-based skin care formulations which are essentially free of surfactants, on the other hand, may resist rinsing, but can form a relatively thick and aesthetically unpleasing layer of oil on the skin.

There is a need for a skin care formulation which can be applied when the skin is wet, e.g., in the shower or bath, but which can be substantially rinsed off while leaving sufficient moisturizing or conditioning agent to protect the skin and provide a long-lasting moisturizing effect.

SUMMARY OF THE INVENTION

The present invention provides skin care formulations which can be administered in the bath or shower, depositing a thin layer of moisturizing or other conditioning agents on application, which is not rinsed off but remains to protect the skin from drying, resulting in smoother, softer skin feel. The formulations of the invention comprise polyvalent metal cations and long chain acids, which react on application in the shower or bath to form a thin deposit of insoluble salts, thereby enhancing the retention of moisturizing oils and conditioning agents.

DETAILED DESCRIPTION OF THE INVENTION

The invention provides a skin care formulation comprising
(i) cosmetically acceptable polyvalent metal cations (more particularly di- or tri-valent metal cations (for example a cation selected from the group consisting of $Ca^{++}$, $Zn^{++}$, $Mg^{++}$, $Al^{+++}$, and mixtures of any two or more of the foregoing), especially transition metal ions, for example as provided by cosmetically acceptable water soluble salt or salts of such cation or cations (more particularly one or more members selected from the group consisting of calcium chloride, zinc citrate, zinc chloride, zinc oxide, zinc acetate, magnesium sulfate, and mixtures of two or more of the foregoing); preferably being present in the form of the salt in an amount of from 0.01 to 2% by weight of the total formulation;
(ii) cosmetically acceptable long chain acids capable of forming an insoluble salt with the polyvalent metal cation (particularly a transition metal cation), with examples of such long chain acids being straight or branched chain saturated or unsaturated fatty acids having 12-40 carbons, particularly $C_{16-30}$ saturated fatty acids, and particular examples including one or more of palmitic acid, stearic acid, or cerotic acid; amounts of such long chain fatty acids being preferably in the range of 2 to 10% by weight of the total formulation;
(iii) a cosmetically acceptable water-insoluble oil component in addition to the long chain fatty acid listed in (ii), particularly a member selected from the group consisting of:
  a. cosmetically acceptable hydrocarbon oils, for example, mineral oil, petrolatum, hydrocarbons found in beeswax (for example, $C_{21-37}$ hydrocarbons), and mixtures of any of the foregoing, especially mixtures of from 1:1 to 3:1 mineral oil to petroleum by weight;
  b. esters of fatty acids and long straight chain alcohols, for example as found in beeswax and polar wax, for example esters of straight chain $C_{24-36}$ alcohols and $C_{18-36}$ fatty acids, such as triacontanol hexadecanoate, hexacosanol hexacosanoate, and myricyl palmitate;
  c. and optionally, lipophilic emollients, e.g.,
    (i) long straight chain alcohols, e.g., C12-34 straight chain alcohols, for example one or more of cetyl alcohol, steryl alcohol, and alcohols found in beeswax and polarwax; and/or
    (ii) silicone oils, for example dimethyl polysiloxane.
  e.g., the oil component being preferably present in an amount of from 25-60% by weight of the total formulation;
wherein the polyvalent metal cation is prevented from substantial reaction with the long chain acid while in the formulation (for example, is in substantially undissolved salt form or is substantially physically sequestered from the long chain acid), but upon application of the formulation to the skin and rinsing with water, is capable of reaction with the long chain acid to form a thin layer of insoluble precipitate on the skin.

By "skin care composition" is meant a composition which provides a therapeutic, prophylactic or cosmetic benefit to the skin, including moisturizing and protecting the skin, thereby improving the condition or health of the skin, including for example water-in-oil and oil-in-water emulsion compositions.

By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration. Heavy metals, radioactive elements, and other materials which one skilled in the art would reasonably expect to be toxic for topical administration are excluded.

The formulation may further comprise:
(i) a hydrophilic component, particularly a member of the group consisting of water and lower alkanols, e.g., alkanols having 2-9 carbons such as ethanol, isopropanol, propylene glycol, glycerol, diglycerol, triglycerol, and mixtures of any of the foregoing; and
(ii) one or more surfactants, e.g., cosmetically acceptable nonionic surfactants so as to form an emulsion with the above-mentioned fatty acids and hydrocarbon oil, e.g., a water-in-oil emulsion or oil-in-water emulsion, preferably a water-in-oil emulsion Surfactants for the emulsion formulations of the invention may comprise a combination of nonionic surfactants, for example, one or more surfactants selected from the group consisting of:
(i) lipophilic surfactants, e.g., having an HLB value of 8 or lower, for example sorbitan-fatty acid esters, such as sorbitan oleates, for example, sorbitan sesquioleate; and
(ii) hydrophilic surfactants, e.g., having an HLB of greater than 8, particularly
  a. di- or tri-alkanol amines, such as triethanol amine;
  b. polyethoxylated surfactants, for example polyethoxylated alcohols (esp. polyethoxylated polyols), polyethoxylated vegetable oils, and polyethoxylated silicones, e.g., polysorbate 80, dimethicone polyethylene oxide, and dimethylmethyl (polyethylene oxide) siloxane.

For a water-in-oil emulsion, the overall HLB of the surfactant mixture is preferably 2-8, i.e., there is typically a higher proportion of lipophilic surfactant; whereas for an oil-in-water emulsion, the overall HLB of the surfactant mixture is preferably 8-16.

The formulation may further comprise preservatives, e.g., chelaters (for example edetic acid (EDTA)), antibacterials, (for example dimethyl-dimethyl-hydantoin (DMDMH)) and/or anti-oxidants (for example tocopheryl acetate); perfumes; coloring agents; and/or other excipients as known in the cosmetic art. For example, the formulation may further comprise pharmaceutically or cosmetically active agents which provide a cosmetic, therapeutic or prophylactic benefit to the skin, for example
(i) skin soothing/conditioning agents, especially plant extracts, e.g. shea butter, aloe vera extract, sweet almond oil, coconut oil; plant essential oils, e.g., lavender oil, rosemary oil, or chamomile extract;
(ii) vitamins, e.g., B complex vitamins such as panthenol, pantothenic acid and their cosmetically acceptable salts, esters and derivatives; or free radical scavenger vitamins in addition to the anti-oxidants provided to stabilize the formulation above, e.g., vitamin C, vitamin E, and their cosmetically acceptable salts, esters and derivatives;
(iii) antibacterials, for example dimethyl-dimethyl-hydantoin (DMDMH), trichlocarban (TCC), or triclosan;
(iv) sun-screen agents, for example p-aminobenzoic acid and its cosmetically acceptable salts, esters and derivatives, as well as sunscreen agents selected from cinnamates, benzophenes and anthranilates.

The pharmaceutically or cosmetically active agent is provided in an effective amount, which will vary depending on the agent selected and the benefit desired, e.g., from 0.1 to 5%.

As noted above, this formulation may further comprise preservatives, e.g., chelaters (for example edetic acid (EDTA)), antibacterials, (for example dimethyl-dimethyl-hydantoin (DMDMH)) and/or anti-oxidants (for example tocopheryl acetate); perfumes; coloring agents; and/or other excipients as known in the cosmetic art.

It will be recognized by one skilled in the art that the thin residue left on the skin following application of the formulations of the invention can be exploited to permit sustained delivery of skin benefit agents, as well as pharmaceutical agents, particularly lipophilic agents which will be deposited on the skin, as well as the moisturizing oils of the formulation. In this aspect the invention provides, for example a method of moisturizing, protecting and/or conditioning the skin comprising applying a formulation of the invention to the skin and rinsing with water, and a method of delivering a pharmaceutically or cosmetically active agent to the skin comprising applying a skin care formulation as described herein, wherein the formulation comprises an effective amount of the pharmaceutically or cosmetically active agent.

Prior to application of the formulation, the polyvalent metal cation is prevented from substantial reaction with the long chain acid while in the formulation, e.g., the cation may be present in substantially undissolved salt form or the cation may be substantially physically sequestered from the long chain acid. Upon application of the formulation to the skin and rinsing with water, the cation is capable of reaction with the fatty acid to form a thin layer of insoluble precipitate on the skin. Reaction of the cation with the long chain acid prior to application can therefore be minimized or prevented, for example,
(i) by encapsulating or coating the cosmetically acceptable salt(s) or the long chain acid(s) such that the capsule or coating is released on application of the formulation, in the presence of water and scrubbing, for example encapsulating in water-soluble capsules, for example starch or water-soluble polymer capsules which or by coating with a meltable coating, e.g., mixing the salt with molten wax, then cooling and pulverizing the mixture, so that the salt particles are coated with a wax coating which is stable in the formulation but dispersed and dissolved on application in the presence of water;
(ii) by utilizing a low-water or nonaqueous formulation, particularly containing less than 20% and, more particularly containing less than 10% of water by weight, in order to prevent substantial solubilization of the cosmetically acceptable salt prior to application, so that the cation is not free to react with the fatty acid prior to application; or
(iii) by adding the cosmetically acceptable salt to a formulation after the oil and aqueous components have been substantially combined, such that either the cosmetically acceptable salt is not substantially dissolved and available for reaction with the acid (for example, when the salt is added to the oil phase of an existing water-in-oil emulsion), or the acid is already sequestered in the oil phase and therefore unavailable for reaction with the cation (for example, when the salt is added to an existing oil-in-water emulsion).

The concentration of the polyvalent metal cation in the formulation of the invention is preferably low, for example, less than 2%, e.g., 0.01-2%, more particularly 0.05-1%, by weight of the cosmetically acceptable salt to the finished formulation, as a small amount is sufficient to permit retention of the moisturizing agents, while very high amounts may leave an aesthetically undesirable film on the skin. When less soluble salts are used or where the water content of the formulation is relatively low, the salt concentration can be somewhat higher while retaining the desirable properties of the formulation, but the concentration should generally not exceed 2% by weight. Anions which are chelating agents can tend to inhibit the formation of the metal salt of the fatty acid, since the formation constant of the metal chelate is typically greater than that of the metal salt of the fatty acid, therefore if chelating agents are used in the formulation, for example as preservatives, weaker chelators such as EDTA are preferred, with the concentration kept to a relatively low level, particularly less than 0.5% and, more particularly, on the order of 0.05-0.15%, and/or the formulation is preferably designed to avoid substantial reaction between the cations and the chelator prior to application, e.g., analogous to the approaches described above to prevent substantial reaction between the fatty acid and the cation prior to application, for example by sequestering the cation from the chelator or preventing substantial dissolution of the salt of the cation in the formulation prior to application.

In one embodiment, the invention provides a skin care product comprising, by weight:
(i) 0.01 to 2%, e.g., 0.05 to 1%, cosmetically acceptable salt of polyvalent metal ion as described above;
(ii) 2 to 10% of one or more long chain fatty acids as described above;
(iii) 25-60% of a cosmetically acceptable oil component as described above;
wherein the cosmetically acceptable water soluble salt is prevented from reacting with the fatty acid prior to application.

In another embodiment, the invention provides a moisturizing composition which is an emulsion, particularly a water-in-oil emulsion, comprising
(i) 0.01-2%, e.g. 0.5 to 1% cosmetically acceptable, water soluble salt of polyvalent metal ion as described above;
(ii) 2-10% fatty acid as described above;
(iii) 25-60% cosmetically acceptable oil component as described above;
(iv) 3-10% surfactant, preferably nonionic surfactant; and
(v) 30-60% hydrophilic component as described above;
wherein the cosmetically acceptable water soluble salt is added after the emulsion has been formed.

For example, in one preferred embodiment, the formulation is a water-in-oil emulsion, comprising
(i) one or more fatty acids as described above (particularly in an amount of 1-4%);
(ii) a cosmetically acceptable oil component as described above (particularly in an amount of 10-40%);
(iii) a hydrophilic component as described above (particularly in an amount of 30-50%); and
(iv) one or more surfactants, preferably nonionic surfactants (particularly in an amount of 3-10%);

and further comprising a cosmetically acceptable salt of a polyvalent metal cation, preferably in an amount of 0.01 to 2%, e.g. 0.05 to 1%, which has been added after the emulsion has been formed.

In a particularly preferred embodiment, the formulation is a water-in-oil emulsion comprising by weight:
(i) 0.05-1% of a cosmetically acceptable salt of a polyvalent metal ion selected from the group containing calcium chloride, zinc citrate, zinc chloride, zinc oxide, zinc acetate, and magnesium sulfate;
(ii) 1-8% of $C_{16-30}$ saturated fatty acids, for example one or more selected from palmitic acid, stearic acid, cerotic acid, and mixtures thereof, preferably stearic acid.
(iii) 2-10% beeswax, polarwax, or mixtures thereof, preferably beeswax;
(iv) 20-30% mineral oil;
(v) 5-20% petrolatum;
(vi) 0.5-5% C12-34 straight chain alcohols, for example, cetyl alcohol, stearyl alcohol or mixtures thereof;
(vii) 30-45% deionized water;
(viii) 2-10% propylene glycol, glycerine or mixtures thereof;
(ix) 2-5% lipophilic surfactant, for example, sorbitan sesquioleate;
(x) 1-3% hydrophilic surfactant, for example, one or more members selected from di- or tri-alkanol amine, polyethoxylated alcohol, polyethoxylated silicone, particularly one or more members selected from triethanol amine, polysorbate 80, and dimethyl methyl (polyethylene oxide) siloxane;
(xi) 0.1-1% preservatives and anti-oxidants, for example, one or more selected from EDTA, DMDMH, and tocopherol acetate;
wherein the cosmetically acceptable salt has been added after the emulsion is already formed;
wherein the formulation optionally further comprises one or more components selected from:
(i) 0.1-2% fragrance;
(ii) 0.05-0.5% colorant;
(iii) 0.1-5% skin benefit agent as described above, e.g., selected from skin soothing agents, vitamins, antibacterials, sunscreen agents and combinations thereof; for example, shea butter, particularly in an amount of 1.5-2.5%.

In a further embodiment, the invention provides a process for preparation of a skin moisturizing formulation according to the invention, as described above, comprising adding the water soluble salt of polyvalent metal ion as described above, to an emulsion, e.g., a water-in-oil emulsion or an oil-in-water emulsion, as described above.

For example, the invention provides a process for preparation of a skin moisturizing formulation which is a water-in-oil emulsion comprising
(i) mixing the aqueous components of the formulation as described above, exclusive of the salt, for example one or more of water, propylene glycol, glycerol, diglycerol and/or triglycerol, together with one or more hydrophilic surfactants; and separately mixing the lipophilic components as described above, for example the long chain acid and oil components, together with one or more lipophilic surfactants, at an elevated temperature, e.g., 60-95 degrees C.;
(ii) adding the aqueous mixture to the lipophilic mixture and homogenizing to form a water-in-oil emulsion;
(iii) cooling the emulsion, e.g., to a temperature in the range of 20-50 degrees C.;
(iv) adding to the emulsion the salt of the polyvalent metal ion and mixing so that the salt is suspended in the oil phase of the water-in-oil emulsion.

The formulations provided herein are based on ingredients used to make the formulation. It will be apparent to one skilled in the art that in some cases the component ingredients may overlap, e.g., beeswax contains long chain alcohols and fatty acids, as well as esters thereof, sorbitan sequioleate may contain oleic acid as an impurity or degradation product, and so forth.

EXAMPLES

The following examples are intended to illustrate the invention, not to limit it, and such variations on these exemplified formulations as would be evident to one skilled in the art are within the scope of this invention.

Examples 1, 1A-1G, 2, 2A, 3 and 3A

Water-in-Oil Emulsions

TABLE 1

| Ingredients | 1 | 1A | 1B | 1C | 1D | 1E | 1F | 1G | 2 | 2A | 3 | 3A |
|---|---|---|---|---|---|---|---|---|---|---|---|---|
| DI Water | 38.15 | 38.05 | 38.02 | 35.26 | 38.05 | 38.05 | 38.05 | 37.85 | 38.15 | 38.04 | 37.1 | 37 |
| EDTA | 0.1 | 0.1 | 0.1 | 0.1 | 0.1 | 0.1 | 0.1 | 0.1 | 0.1 | 0.1 | 0.1 | 0.1 |

TABLE 1-continued

| Ingredients | 1 | 1A | 1B | 1C | 1D | 1E | 1F | 1G | 2 | 2A | 3 | 3A |
|---|---|---|---|---|---|---|---|---|---|---|---|---|
| Tween 80 | 0.2 | 0.2 | 0.2 | 0.2 | 0.2 | 0.2 | 0.2 | 0.2 | 0.2 | 0.2 | 0.2 | 0.2 |
| Propylene Glycol | 5 | 5 | 5 | 5 | 5 | 5 | 5 | 5 | 5 | 5 | 5 | 5 |
| Glycerine | | | | | | | | | | | | |
| Triethanolamine | 0.5 | 0.5 | 0.5 | 0.5 | 0.5 | 0.5 | 0.5 | 0.5 | 0.5 | 0.5 | 0.5 | 0.5 |
| Shea butter | 2 | 2 | 2 | 2 | 2 | 2 | 2 | 2 | 2 | 2 | 2 | 2 |
| White beeswax | 5 | 5 | 5 | 5 | 5 | 5 | 5 | 5 | 5 | 5 | 5 | 5 |
| Polawax | | | | | | | | | | | | |
| Stearic acid | 2.5 | 2.5 | 2.5 | 2.5 | 2.5 | 2.5 | 2.5 | 2.5 | 2.5 | 2.5 | 2.5 | 2.5 |
| Sorbitan sesquioleate | 3 | 3 | 3 | 3 | 3 | 3 | 3 | 3 | 3 | 3 | 3 | 3 |
| Mineral oil | 23.95 | 23.95 | 23.95 | 23.95 | 23.95 | 23.95 | 23.95 | 23.95 | 23.95 | 23.95 | 23.95 | 23.95 |
| Dimethyl polysiloxane | | | | | | | | | | | 4 | 4 |
| Dimethyl, methyl(polyethylene oxide)siloxane | 1 | 1 | 1 | 1 | 1 | 1 | 1 | 1 | 1 | 1 | 1 | 1 |
| Petrolatum | 15 | 15 | 15 | 15 | 15 | 15 | 15 | 15 | 10 | 10 | 6 | 6 |
| Cetyl stearyl alcohol | 2.5 | 2.5 | 1.5 | 2.5 | 2.5 | 2.5 | 2.5 | 2.5 | 1.5 | 1.5 | 2.5 | 2.5 |
| Fragrance | 0.5 | 0.5 | 0.5 | 0.5 | 0.5 | 0.5 | 0.5 | 0.5 | 0.5 | 0.5 | 0.5 | 0.5 |
| DMDMH | 0.5 | 0.5 | 0.5 | 0.5 | 0.5 | 0.5 | 0.5 | 0.5 | 0.5 | 0.5 | 0.5 | 0.5 |
| Tocopherol acetate | 0.1 | 0.1 | 0.1 | 0.1 | 0.1 | 0.1 | 0.1 | 0.1 | 0.1 | 0.1 | 0.1 | 0.1 |
| CaCl2.2H2O | | 0.10 | 0.13 | 2.89 | | | | | | 0.11 | | 0.1 |
| Zinc citrate | | | | | 0.1 | | | | | | | |
| Zinc chloride | | | | | | 0.1 | | | | | | |
| MgSO4 | | | | | | | 0.1 | | | | | |
| Zinc oxide | | | | | | | | | | | | |
| Total | 100 | 100 | 100 | 100 | 100 | 100 | 100 | 100 | 100 | 100 | 100 | 100 |

The amounts in the table above are given as a weight percentage of the final formulation.

The above formulations are prepared as water-in-oil emulsions, and the metal salts added once the emulsion is complete. The metal salts are substantially undissolved in the continuous (oil) phase of the emulsions.

Formulations 1A-1G, and 2A are prepared as follows:

Part A (Water Phase)

Add water in a side vessel and begin to stir and heat;

Add EDTA; mix and heat:

Add Polysorbate 80 (Tween 80); continue to mix and heat:

Add Propylene Glycol; continue to mix and heat:

Add Triethanolamine; continue to mix and heat:

Continue to mix and heat until a temperature of 80° C. is reached

Part B (Oil Phase)

To main vessel, add Shea Butter

Add White Beeswax

Add Stearic Acid

Add Sorbitan Sesquioleate

Add Mineral Oil

Add DC 193 Fluid

Add Petrolatum

Add Cetyl Stearyl Alcohol

Add Vitamin E Acetate

Heat and mix until homogenous and a temperature of 80° C. is reached

Part C

When both phases have reached 80° C., add water phase to oil phase and homogenize. After homogenization, begin cooling process. When a temperature of 38° C. is reached, add DMDM Hydantoin and fragrance. Disperse metal salt. Continue mixing until homogenous.

Formulations 1 and 2 (comparative examples) are prepared in the same way, except that there is no metal salt added. Formulation 3 and 3A are prepared in the same way, except that the silicone oil (dimethylpolysiloxane) is included in the oil phase, and in formulation 3, there is also no metal salt.

The formulations are compared on the basis of consistency and skin feel. Formulations 1A, 1B, 2A, 3A, 1D, 1E, 1F and 1G are found to have superior consistency and to provide enhanced silky skin feel compared to Formulations 1, 2, and 3, which do not have the added metal salts, and compared to formulation 1C, which has a relatively high level of added metal salt.

Examples 4 and 4A

Oil-in-Water Emulsions

| Ingredient | Example 4 | Example 4A |
|---|---|---|
| Deionized water | 48.85 | 45.55 |
| Triethanolamine | 2.00 | 2.00 |
| White Beeswax | 5.00 | 5.00 |
| Stearic acid (Emersol 153) | 6.00 | 6.00 |
| Mineral oil (Drakeol 6) | 23.00 | 23.00 |

-continued

| Ingredient | Example 4 | Example 4A |
|---|---|---|
| Glyceryl oleate (Monumols 90-018) | 0.50 | 0.50 |
| Snow white petrolatum | 15.00 | 15.00 |
| Shea butter | 2.00 | 2.00 |
| Fragrance | 0.40 | 0.40 |
| DMDM Hydantoin | 0.25 | 0.25 |
| Zinc oxide | | 0.30 |
| Total | 100 | 100 |

The amounts in the table above are given as a weight percentage of the final formulation.

The above formulations are prepared as oil-in-water emulsions, and the metal salt (here, zinc oxide) is added once the emulsion is complete. The metal salt does not enter the oil phase of the emulsions to any significant degree and thus does not react with the fatty acids. The formulations are prepared as follows:

Part A (Water Phase)

Add water to a main vessel and begin to stir and heat;

Add Triethanolamine and continue to mix and heat until a temperature of 80° C. is reached Part B (Oil Phase)

To a side vessel, add Shea Butter

Add White Beeswax

Add Stearic Acid

Add Glyceryl oleate

Add Mineral Oil

Add Petrolatum

Heat and mix until homogenous and a temperature of 80° C. is reached

Part C

When both phases have reached 80° C., slowly add oil phase to water phase and homogenize. After homogenization, cool while stirring. When temperature drops below 40° C., add DMDM Hydantoin and fragrance. Disperse zinc oxide for formulation 4A. Continue mixing until homogenous.

The formulations are compared on the basis of consistency and skin feel. Formulation 4A is found to have superior consistency and to provide enhanced silky skin feel compared to Formulation 4, which does not have an added metal salt.

The invention claimed is:

1. A skin care formulation comprising:
   (i) cosmetically acceptable polyvalent metal cations;
   (ii) cosmetically acceptable C12-C40 fatty acid capable of forming an insoluble salt with the polyvalent metal cation;
   (iii) a cosmetically acceptable water-insoluble oil component;
   wherein the polyvalent metal cation is prevented from reaction with the fatty acid while in the formulation, but upon application of the formulation to the skin and rinsing with water, is capable of reaction with the fatty acid to form a thin layer of insoluble precipitate on the skin.

2. The formulation of claim 1 wherein the polyvalent metal cations are selected from the group consisting of $Ca^{++}$, $Zn^{++}$, $Mg^{++}$, $Al^{+++}$, and combinations of any two or more of these.

3. The formulation of claim 1 wherein the polyvalent metal cations are provided in the form of a cosmetically acceptable water soluble salt.

4. The formulation of claim 3 wherein the salts are selected from the group consisting of calcium chloride, zinc citrate, zinc chloride, zinc oxide, zinc acetate, magnesium sulfate, and combinations of any two or more of these.

5. The formulation of claim 1 wherein the fatty acids are saturated fatty acids.

6. The formulation of claim 5 wherein the fatty acids include one or more selected from the group consisting palmitic acid, stearic acid, or cerotic acid.

7. The formulation of claim 1 wherein the cosmetically acceptable water insoluble oil component comprises one or more ingredients selected from the group consisting of (i) cosmetically acceptable hydrocarbon oils and (ii) esters of fatty acids and long straight chain alcohols.

8. The formulation of claim 1 wherein the cosmetically acceptable water insoluble oil component comprises one or more ingredients selected from the group consisting of mineral oil, petroleum, beeswax and polar wax.

9. The formulation of claim 3 wherein the cosmetically acceptable salt(s) or the fatty acid(s) is coated or encapsulated.

10. The formulation of claim 1 comprising less than 20% water by weight.

11. The formulation of claim 3 wherein the salt is added to the formulation after the oil and aqueous components have been combined.

12. The formulation of claim 1 wherein the skin care formulation is an emulsion.

13. The formulation of claim 12 which is a water-in-oil emulsion.

14. The formulation of claim 13 which comprises a mixture of surfactants having a combined HLB of less than 8.

15. The formulation according to claim 3 comprising by weight
   (i) 0.01 to 2% cosmetically acceptable water soluble salt of polyvalent metal ion;
   (ii) 2 to 10% of fatty acids;
   (iii) 25-60% cosmetically acceptable oil component;
   wherein the cosmetically acceptable water soluble salt is prevented from reacting with the fatty acid prior to application.

16. The formulation according to claim 1 which is a water-in-oil emulsion comprising by weight
   (i) 0.05-1% of a cosmetically acceptable salt of a polyvalent metal ion selected from the group containing calcium chloride, zinc citrate, zinc chloride, zinc oxide, zinc acetate, and magnesium sulfate;
   (ii) 1-80% of $C_{16-30}$ saturated fatty acids
   (iii) 2-10% beeswax, polarwax, or mixtures thereof
   (iv) 20-30% mineral oil;
   (v) 5-20% petrolatum;
   (vi) 0.5-5% $C_{12-34}$ straight chain alcohols;
   (vii) 30-45% deionized water;
   (viii) 2-10% propylene glycol, glycerine or mixtures thereof
   (ix) 2-5% lipophilic surfactant;
   (x) 1-3% hydrophilic surfactant;
   (xi) 0.1-1% preservatives and/or anti-oxidants;
   wherein the cosmetically acceptable salt has been added after the emulsion is already formed.

17. The formulation of claim 1 which further comprises one or more of 0.1-2% fragrance and/or 0.05-0.5% colorant.

18. The formulation of claim 1 further comprising a pharmaceutically or cosmetically active agent selected from skin soothing agents, vitamins, antibacterial agents, sunscreen agents, and combinations thereof.

19. The formulation of claim 18 wherein the pharmaceutically or cosmetically active agent is a skin soothing agent.

20. The formulation of claim 19 wherein the skin soothing agent is shea butter.

21. A process for preparation of a skin care formulation as described in claim 1 comprising preparing an emulsion comprising hydrophilic components, lipopilic components and surfactants, and adding a water soluble salt of polyvalent metal ion to the emulsion.

22. The process of claim 21 wherein the skin care formulation is a water-in-oil emulsion and the process comprises
(i) mixing the water soluble components of the formulation, exclusive of the salt, together with one or more hydrophilic surfactants; and separately mixing the lipophilic components, together with one or more lipophilic surfactants, at a temperature wherein the components are liquid;
(ii) adding the mixture of water soluble components to the lipophilic mixture and homogenizing to form a water-in-oil emulsion;
(iii) cooling the emulsion;
(iv) adding to the emulsion the salt of the polyvalent metal ion and mixing so that the salt is suspended in the oil phase of the water-in-oil emulsion.

23. A skin care formulation prepared by the process of claim 22.

24. A method comprising applying a skin care formulation of claim 1 to skin and rinsing with water.

* * * * *

UNITED STATES PATENT AND TRADEMARK OFFICE

CERTIFICATE OF CORRECTION

| | | |
|---|---|---|
| PATENT NO. | : 7,807,189 B2 | Page 1 of 1 |
| APPLICATION NO. | : 10/976100 | |
| DATED | : October 5, 2010 | |
| INVENTOR(S) | : Hassan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1676 days.

Signed and Sealed this
Tenth Day of May, 2011

David J. Kappos
*Director of the United States Patent and Trademark Office*